United States Patent [19]
Nakano

[11] Patent Number: 5,568,254
[45] Date of Patent: Oct. 22, 1996

[54] LOW PRESSURE DISCHARGE TUBE AND ATOMIC ABSORPTION SPECTROPHOTOMETER USING THE SAME

[75] Inventor: Tomohiro Nakano, Kyoto, Japan

[73] Assignee: Shimadzu Corporation, Japan

[21] Appl. No.: 10,328

[22] Filed: Jan. 28, 1993

[30] Foreign Application Priority Data

Jan. 31, 1992 [JP] Japan ................... 4-046065

[51] Int. Cl.⁶ .................................................. G01J 3/42
[52] U.S. Cl. ............................................ 356/307; 356/312
[58] Field of Search .................................. 356/307, 311, 356/312; 313/15, 44, 609, 611, 607

[56] References Cited

U.S. PATENT DOCUMENTS

| | | | |
|---|---|---|---|
| 4,032,235 | 6/1977 | Kiefer et al. | 356/307 |
| 4,100,446 | 7/1978 | Harada et al. | 356/311 |
| 4,140,385 | 2/1979 | Shaw et al. | 313/15 X |
| 4,377,342 | 3/1983 | Koizumi et al. | 356/307 |
| 4,645,343 | 2/1987 | Stockdale et al. | 356/312 |
| 4,877,997 | 10/1989 | Fein | 313/634 |
| 4,948,250 | 8/1990 | Oishi et al. | 356/307 |
| 5,181,077 | 1/1993 | Dencks | 356/307 |

FOREIGN PATENT DOCUMENTS

| | | | |
|---|---|---|---|
| 771173 | 10/1934 | France . | |
| 1158700 | 6/1958 | France | 313/611 |
| 3005638 | 8/1981 | Germany . | |
| 0119739 | 5/1989 | Japan | 356/311 |

*Primary Examiner*—K. Hantis
*Attorney, Agent, or Firm*—Klima & Hopkins, P.C.

[57] ABSTRACT

In an atomic absorption spectrophotometer utilizing the direct Zeeman's method, plural lamps are installed in the light source unit in order to enhance the versatility and enable continuous analyses. Accordingly, a plurality of low pressure discharge tubes 14 and hollow cathode lamps 16 in total are mounted on a lamp holder 12 of the light source unit, and by rotating the lamp holder 12, an arbitrary lamp may be positioned at the light source position for measurement. When the low pressure discharge tube 14 is used as the light source, in order to perform background correction by the Zeeman's method, a permanent magnet or an electromagnet 24 for operating a magnetic field on the light source is disposed, and a polarizing unit 26 is disposed on the measurement optical path, so that the direction of polarization of the measurement light to be sent to an atomizing unit 26 is changed over between the atomic absorption measurement mode and the background correction mode.

10 Claims, 3 Drawing Sheets

LOW PRESSURE DISCHARGE TUBE AND ATOMIC ABSORPTION SPECTROPHOTOMETER USING THE SAME

BACKGROUND OF THE INVENTION

1. Field of the Invention

The invention relates to an atomic absorption spectrophotometer for quantitating metal elements contained in sample substance, and a low pressure discharge tube used as the light source for the atomic absorption spectrophotometer.

2. Description of the Prior Art

A hollow cathode lamp is generally used as the light source for an atomic absorption spectrophotometer, but a low pressure discharge tube is also used. The low pressure discharge tube is, as shown in FIG. 1, a U-shaped enclosed light permeable lamp tube 2, in which metal or metal salt 4 such as halide is sealed in an evaporable state together with rare gas such as argon. The argon is sealed in at a pressure of, for example, 40 mmHg. In the curved part of the lamp tube 2, a part for storing the metal or metal salt 4 is provided, and electrodes 6a, 6b are put in the lamp tube 2 from the base part of the straight portion of the lamp tube 2. A heater wire 8 for stabilizing the lighting of the lamp is wound around the lamp tube 2.

The luminescence of the low pressure discharge tube emitted in the direction orthogonal to the straight portion within the plane containing the straight portion is utilized. Accordingly, if the lamp intensity is strengthened, the light from the preceding straight portion is absorbed by the succeeding straight portion, and the output light intensity is not so strong, and the analytical sensitivity is not enhanced so much.

In the atomic absorption analysis, as the method for correcting the background, three types are known, that is, the $D_2$ (Deuterium) method, the self-resorption method (SR method), and the Zeeman's method. In the $D_2$ method, a hollow cathode lamp and $D_2$ lamp are used as the light source, and in the self-resorption method, the discharge current value is changed only by the hollow cathode lamp. The Zeeman's method is roughly classified into the direct Zeeman's method and absorption beam Zeeman's method. In the direct Zeeman's method, an exclusive low pressure discharge tube is used as the light source. The direct Zeeman's method makes use of the phenomenon of wavelength separation of the light radiated from the light source placed in a magnetic field due to the Zeeman effect.

In the case of direct Zeeman's method, when the low pressure discharge tube in FIG. 1 is used, the hollow cathode lamp cannot be installed in its light source. Accordingly, only limited elements can be analyzed by the atomic absorption spectrophotometer according to the direct Zeeman's method.

In the direct Zeeman's method, moreover, since the light source must be placed in the magnetic field, only one type of lamp can be mounted.

In the atomic absorption spectrophotometer according to the direct Zeeman's method, since the light source is a low pressure discharge tube in the shape shown in FIG. 1, and the number of elements that can be analyzed is small, and the versatility is poor.

Yet, since only one lamp can be installed in the light source unit, it is impossible to operate to analyze sequentially and continuously by changing samples.

In the shape as shown in FIG. 1, still more, the emission intensity cannot be strengthened so much, and it is hard to raise the analytical sensitivity (S/N ratio).

SUMMARY OF THE INVENTION

It is hence a primary object of the present invention to enhance the versatility and enable continuous analysis by increasing the number of elements that can be analyzed and installing plural lamps in the light source unit, in an atomic absorption spectrophotometer capable of correcting the background at least by making use of the direct Zeeman's method.

It is other object of the present invention to present a low pressure discharge tube suited to be used as a light source in an atomic absorption spectrophotometer for correcting the background by making use of the direct Zeeman's method.

The discharge tube suited to correct the background by making use of the Zeeman's method used in the present invention is a low pressure discharge tube comprising a U-shaped enclosed light permeable lamp tube sealed with a metal or metal salt in an evaporable state together with a rare gas, so that the luminescence emitted in a direction parallel to the straight portion in the outward direction from the curved portion of the lamp tube is utilized.

In the atomic absorption spectrophotometer of the present invention using such discharge tube, a plurality of lamps are installed in the lamp holder of the light source unit, and an arbitrary lamp can be positioned at the light source position for measurement, and at least one of the lamps installed in the lamp holder is a low pressure discharge tube comprising a U-shaped enclosed light permeable lamp tube sealed with a metal or metal salt in an evaporable state together with a rare gas, so as that the luminescence emitted in a direction parallel to the straight portion in the outward direction from the curved portion of the lamp tube is utilized, and the light source unit comprises a magnetic field generating part for operating a magnetic field in the low pressure discharge tube at the light source position for measurement, while a polarizing unit for changing over the direction of polarization is disposed in the measurement optical path from the light source for measurement to the detecting part.

In the low pressure discharge tube of the invention, since the luminescence emitted in a direction parallel to the straight portion in the outward direction from the curved portion of the lamp tube is utilized, the self-absorption of light is less, and the emission intensity is increased, so that the analytical sensitivity may be enhanced.

By using the light emitted in the outward direction from the curved portion, plural lamps including the low pressure discharge tube may be mounted on a common lamp holder. If two or more types of low pressure discharge tubes can be mounted on the lamp holder, two or more elements may be measured by making use of the background correction method by the Zeeman's method.

When at least one low pressure discharge tube and at least one hollow cathode lamp on the lamp holder, both the background correction by the Zeeman's method and the background correction by the $D_2$ method or self-resorption method may be utilized.

The foregoing and other objects, features, aspects and advantages of the present invention will become more apparent from the following detailed description of the present invention when taken in conjunction with the accompanying drawings.

DESCRIPTION OF THE PREFERRED EMBODIMENT

Figure 1:
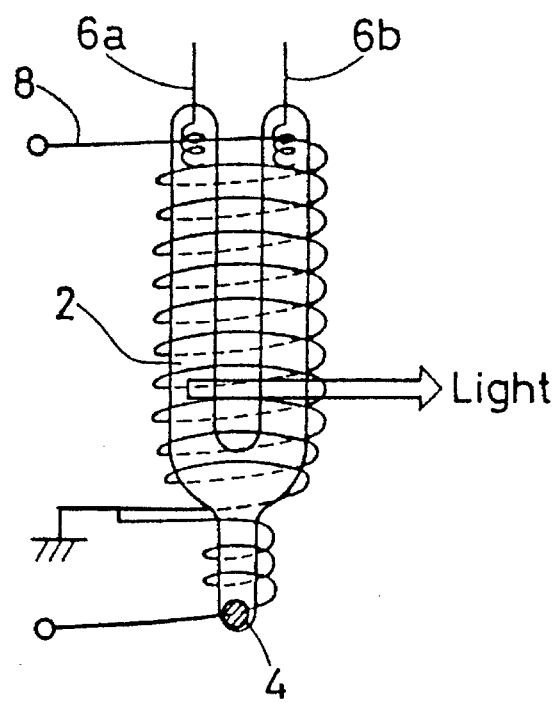
FIG. 1 is a schematic side view showing a conventional low pressure discharge tube.
Figure 2:
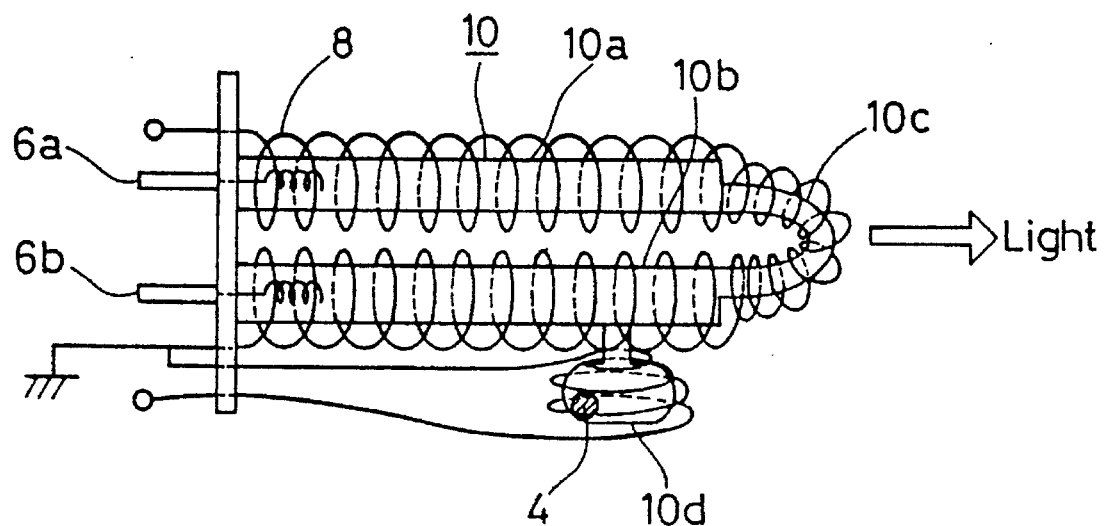
FIG. 2 is a schematic side view showing an embodiment of a low pressure discharge tube of the present invention.

FIG. 2 shows an embodiment of a low pressure discharge tube of the present invention.

A lamp tube 10 is in a U-form on the whole comprising two straight portions 10a, 10b parallel to each other and a curved portion 10c between the straight portions 10a, 10b, and one straight portion 10b is provided with a housing 10d accommodating metal or metal salt 4 such as halide in an evaporable state. The lamp tube 10 is enclosed, and a rare gas such as argon is sealed inside, at a pressure of about 40 mmHg. The diameter of the straight portions 10a, 10b of the lamp tube 10 is greater than the diameter of the curved portion 10c. From the base part of the straight portions 10a, 10b, electrodes 6a, 6b are put into the lamp tube 10. A heater wire 8 for stabilizing the light is wound around the lamp tube 10.

The luminescence emitted, as shown by arrow in FIG. 2, in a direction parallel to the straight portions 10a, 10b in the outward direction from the curved portion 10c. Since the diameter of the curved portion 10c is utilized smaller than that of the straight portions 10a, 10b, the self-absorption of luminescence is restricted smaller, so that the emission strength is further intensified.

Figure 3:
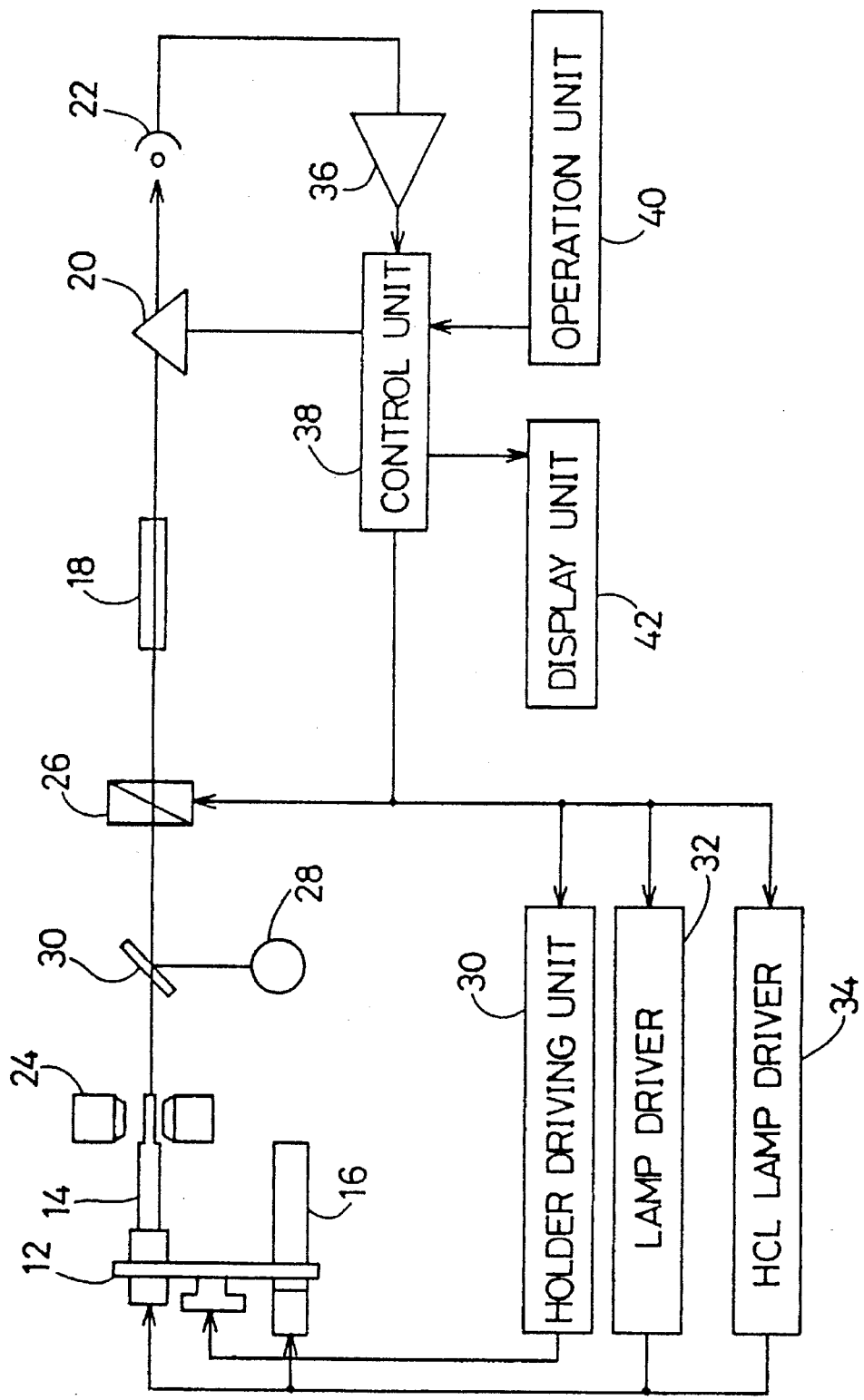
FIG. 3 is a schematic structural diagram showing an atomic absorption spectrophotometer of the present invention.

FIG. 3 schematically shows an embodiment of an atomic absorption spectrophotometer of the present invention.

In the light source unit, at least one low pressure discharge tube 14 according to the present invention and at least one hollow cathode lamp 16 are mounted on a lamp holder 12, and by rotating the lamp holder 12, a desired lamp is positioned at the light source position for measurement. In FIG. 3, the low pressure discharge tube 14 is positioned at the light source position for measurement.

On the optical path of the measurement light from the light source for measurement, an atomizing unit 18 is disposed, and the light penetrating through the atomizing unit 18 is separated in a spectroscopic unit 20 and detected by a detector 22. When the low pressure discharge tube 14 is used as the light source, in order to correct the background by the Zeeman's method, a permanent magnet (or electromagnet) 24 for operating a magnetic field in the light source at the light source position for measurement. The magnet 24 is composed so as to function only when using the low pressure discharge tube 12. When utilizing the Zeeman's method, furthermore, a polarizing unit 26 is disposed on the optical path, and the direction of polarization of the measurement light to be sent to the atomizing unit 18 is changed over between the atomic absorption measurement mode and the background correction mode. Moreover, in order to correct the background by the $D_2$ method when the hollow cathode lamp 16 is used as the light source for measurement, it is designed so that the light from a $D_2$ lamp 28 may be introduced into the measurement optical path by a half mirror 30.

The lamp holder 12 can position a desired lamp at the light source position for measurement by a holder driving unit 30. When the measurement is over with a certain lamp, the lamp holder 12 is driven by the holder driving unit 30, and the next lamp is set at the light source position for measurement. A lamp driver 32 is connected to the low pressure discharge tube 14, and the lighting of the lamp 14 is controlled, and an HCL lamp driver 34 is connected to the hollow cathode lamp 16, and the lighting of the lamp 16 is controlled. The lamp drivers 32, 34 control the lamps so that the lamp set at the light source position for measurement is lit, and the lamp to be used next is lit preliminarily. Numeral 36 is a signal processing part to take the detection signal of the detector 22 into a control unit 38. The control unit 38 to which an operation unit 40 and a display unit 42 are connected, controls the action of the holder driving unit 30 and lamp drivers 32, 34, the action of the polarizing unit 26, and the wavelength scanning of the spectroscopic unit 20.

A practical example of the light source unit is explained below by reference to FIG. 4 and FIGS. 5A, 5B.

Figure 4:
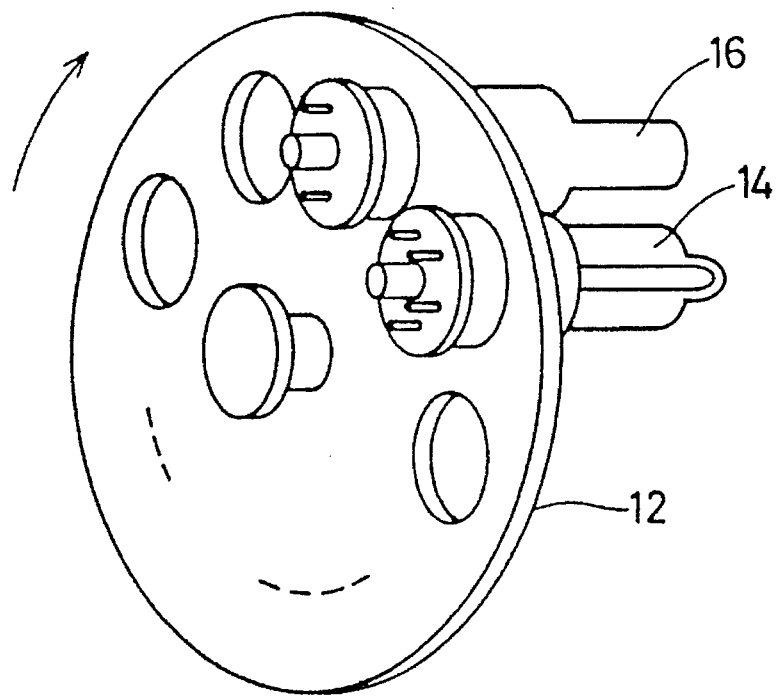
FIG. 4 is a schematic perspective view showing the light source unit in FIG. 3.
Figures 5A, 5B:
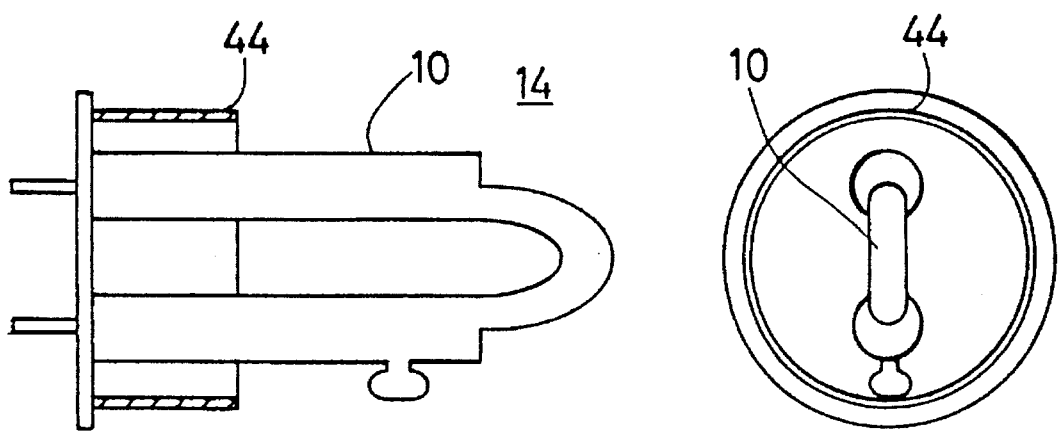
FIG. 5A is a side sectional view showing an example of a low pressure discharge tube mounted on the lamp holder in FIG. 4.
FIG. 5B is a front view of the same.

In FIG. 4, the lamp holder 12 is designed to accommodate a plurality of hollow cathode lamps 16 and low pressure discharge tubes 14, and the luminescence of any lamp is taken out in a direction vertical to the surface of the lamp holder 12. The low pressure discharge tube 14 is in a circular circumferential shape same as the hollow cathode lamp, as shown in FIGS. 5A, 5B, with the lamp tube 10 put in a cylindrical lamp case 44. By putting such lamp tube 10 in the cylindrical lamp case 44, the lamp holder 12 may have a simple structure, having only circular holes as shown in FIG. 4, and low pressure discharge tube 14 can be mounted together with the hollow cathode lamp 16, and mounting of the lamp is as simple as to put the lamp into the hole of the lamp holder 12. In particular, when the outside diameter of the hollow cathode lamp 16 in the portion to be inserted into the hole in the lamp holder 12, and the outside diameter of the lamp case 44 of the low pressure discharge tube are made equal, a plurality of uniform holes for mounting the lamps may be formed in the lamp holder 12, so that the low pressure discharge tubes 14 and hollow cathode lamps 16 may be mounted arbitrarily.

The operation of the atomic absorption spectrophotometer in FIG. 3 is explained below.

When the low pressure discharge tube 14 is selected as the light source, the measurement is done while correcting the background by the Zeeman's method, using the magnet 24 and polarizing unit 26.

When the hollow cathode lamp 16 is selected as the light source, the magnet 24 and polarizing unit 26 are not used. In the case of background correction by self-resorption method, although a discharge current flows into the hollow cathode lamp 16 by means of the HCL lamp driver 34, the measurement is done by changing over the discharge current so as to be a low current when measuring the atomic absorption, and a high current when measuring the background absorption. In the case of $D_2$ method, in atomic absorption measurement, the emission from the hollow cathode lamp 16 is used, while the emission from the $D_2$ lamp 28 is used for measurement of background absorption.

In the light source unit, a plurality of lamps are installed for measuring plural elements so as to contain at least one low pressure discharge tube, and the lamp is selected depending on the element to be measured. A plurality of low pressure discharge tubes only may be installed in the lamp holder 12.

The low pressure discharge tube of the present invention is a U-shaped enclosed light permeable lamp tube, which is sealed with metal or metal salt in an evaporable state together with a rare gas, and is designed that the luminescence emitted in a direction parallel to the straight portion in the outward direction from the curved portion of the lamp tube is utilized, so that the emission strength may be intensified. As a result, samples that could be hardly measured by the conventional atomic absorption spectrophotometer because of low sensitivity can be analyzed by using the low pressure discharge tube of the invention.

Moreover, in the low pressure discharge tube of the present invention, since the light emitted in the same direction as the hollow cathode lamp is utilized, it can be mounted on the common lamp holder together with the hollow cathode lamp, and plural low pressure discharge tubes can be mounted. Hence, multiple elements can be analyzed sequentially and continuously by the atomic absorption spectrophotometer utilizing the direct Zeeman's method, and the number of elements that can be analyzed may be increased, so that a versatile atomic absorption spectrophotometer may be realized.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An atomic absorption spectrophotometer, comprising:

a light source unit for generating measurement light, said light source unit comprising a plurality of lamps including at least one low pressure discharge tube lamp and at least one hollow cathode lamp which are mounted on a surface of a common lamp holder, said light source unit capable of selectively positioning one of said lamps at a light source position for emitting measuring light along an optical path during sample measurement, said light source unit including a magnetic field generating unit for operating a magnetic field on said low pressure discharge tube lamp when located at the light source position, said lamp holder being so arranged that the surface of said lamp holder is perpendicular to an optical path of the measurement light, said low pressure discharge tube comprising a U-shaped enclosed light permeable lamp tube having two straight portions parallel to each other and a curved portion connecting said straight portions, said lamp tube being sealed and containing a metal or metal salt in an evaporable state together with a rare gas, said low pressure discharge tube being so mounted on the surface of said lamp holder that the straight portions are arranged perpendicular to the surface of said lamp holder, and luminescence in a direction parallel to said straight portions and outwardly from said curved portion along the optical path of the measurement light is utilized;

said hollow cathode lamp being so mounted on the surface of said lamp holder that luminescence is emitted along the optical path of the measurement light;

a polarizing unit disposed on the optical path of the measurement light for changing the direction of polarization of the measurement light by 90°;

an atomizing unit located on the optical path of the measurement light;

a spectroscopic unit located on the optical path of the measurement light for separating the measurement light passing through said atomizing unit;

a detector for detecting the measurement light separated by said spectroscopic unit;

a $D_2$ lamp located off the optical path of the measurement light; and a half mirror located on the optical path of the measurement light, said half mirror is located between said light source unit and said atomizing unit, and positioned so that light from said $D_2$ lamp can be directed along the optical path of the measurement light.

2. An atomic absorption spectrophotometer of claim 1, wherein said low pressure discharge tube lamp includes a cylindrical lamp case protecting said lamp tube, said cylindrical lamp case configured to be received in a lamp holder fitting of said lamp holder for releasably connecting said low pressure discharge tube lamp to said lamp holder.

3. An atomic absorption spectrophotometer of claim 2, including:

at least one hollow cathode lamp mounted on said lamp holder, said lamp case of said low pressure discharge tube having an outer diameter equal to an outer diameter of a mounting part of said hollow cathode lamp to allow said low pressure discharge tube and said hollow cathode lamp to be selectively received in different universal lamp holding fittings of said lamp holder.

4. An atomic absorption spectrophotometer of claim 1, wherein said lamp tube includes a receptacle for accommodating said metal or metal salt, said receptacle is disposed in one of said straight portions of said lamp tube.

5. An atomic absorption spectrophotometer of claim 4, wherein said receptacle is located in a lower straight portion of said lamp tube.

6. An atomic absorption spectrophotometer of claim 5, wherein said lamp tube is oriented in a vertical plane with one straight portion positioned above the other straight portion, and said receptacle extends downwardly from said lower straight portion.

7. An atomic absorption spectrophotometer of claim 1, wherein diameters of said straight portions of said lamp tube are greater than a diameter of said curved portion.

8. An atomic absorption spectrophotometer of claim 1, wherein a heater wire is wound around said lamp tube.

9. An atomic absorption spectrophotometer of claim 1, including a control unit and lamp driver for selectively turning on one of said lamps when positioned at said light source position.

10. An atomic absorption spectrophotometer of claim 9, wherein remaining one or more lamps not located at said light source position are turned off by said control unit and lamp driver.

* * * * *